(12) United States Patent
Choi

(10) Patent No.: US 11,766,458 B2
(45) Date of Patent: Sep. 26, 2023

(54) METHOD AND A DIETARY COMPOSITION ON REGULATION, TREATMENT, AND PREVENTION OF OBESITY

(71) Applicant: MyoungSeok Choi, Seoul (KR)

(72) Inventor: MyoungSeok Choi, Seoul (KR)

(*) Notice: Subject to any disclaimer, the term of this patent is extended or adjusted under 35 U.S.C. 154(b) by 95 days.

(21) Appl. No.: 17/513,901

(22) Filed: Oct. 29, 2021

(65) Prior Publication Data

US 2023/0025468 A1    Jan. 26, 2023

(30) Foreign Application Priority Data

Jul. 14, 2021 (KR) .................. 10-2021-0092244

(51) Int. Cl.
| | | |
|---|---|---|
| *A61K 31/00* | (2006.01) | |
| *A61K 35/20* | (2006.01) | |
| *A61K 31/405* | (2006.01) | |
| *A61K 31/198* | (2006.01) | |
| *A61K 9/00* | (2006.01) | |
| *A23L 33/00* | (2016.01) | |
| *A23L 33/175* | (2016.01) | |
| *A23L 33/19* | (2016.01) | |
| *A23P 10/40* | (2016.01) | |
| *A61P 3/04* | (2006.01) | |

(52) U.S. Cl.
CPC ............ *A61K 35/20* (2013.01); *A23L 33/175* (2016.08); *A23L 33/19* (2016.08); *A23L 33/30* (2016.08); *A23P 10/40* (2016.08); *A61K 9/0053* (2013.01); *A61K 31/198* (2013.01); *A61K 31/405* (2013.01); *A61P 3/04* (2018.01); *A23V 2002/00* (2013.01)

(58) Field of Classification Search
CPC ...................................................... A61K 31/00
See application file for complete search history.

(56) References Cited

FOREIGN PATENT DOCUMENTS

WO    WO-2008054200 A2 *   5/2008 ........... A23C 9/1526

OTHER PUBLICATIONS

Soupart et al., "Amino acid composition of human milk," Dept. of Biochemistry and Nutrition, Faculty of Medicine, University of Brussels, Brussels, Belgium, pp. 699-704, 1954.*

* cited by examiner

*Primary Examiner* — Rosanne Kosson
(74) *Attorney, Agent, or Firm* — Revolution IP, PLLC

(57) ABSTRACT

The present invention provides a method and a dietary composition for prevention and regulation of obesity capable of obtaining efficacy such as required appetite suppression or satiety by having a positive effect on concentrations of neurotransmitters such as serotonin, dopamine, and norepinephrine, and GLP-1 which are the principle of a mechanism of appetite inhibitory drugs without prescription of medicines (Phentermine, Prozac, Saxenda, etc.) and further being used as an alternative diet and supplying a protein that is the most lack ingredient during diet. The dietary composition includes tryptophan, which is one amino acid, tyrosine, which is the other amino acid, arginine, which is another amino acid, and a whey protein as active ingredients.

4 Claims, 4 Drawing Sheets

[FIG. 1]

|  | Subject A1 (height=174cm) | | Subject A2 (height=163cm) | | Subject A3 (height=171cm) | | Subject A4 (height=161cm) | | Subject A5 (height=154cm) | |
|---|---|---|---|---|---|---|---|---|---|---|
|  | 0 week | 12 weeks | 0 week | 12 weeks | 0 week | 12 weeks | 0 week | 12 weeks | 0 week | 12 weeks |
| Weight (kg) | 91.3 | 88.6 | 72.4 | 70.2 | 102.3 | 99.5 | 74 | 71.5 | 75.8 | 72.9 |
| PIBW (%) | 143.60 | 139.35 | 129.76 | 125.82 | 166.60 | 162.04 | 135.94 | 131.35 | 152.99 | 147.14 |
| BMI (Kg/m2) | 30.16 | 29.26 | 27.25 | 26.42 | 34.99 | 34.03 | 28.55 | 27.58 | 32.13 | 30.90 |
| Body fat rate (%) | 39.4 | 36.8 | 32.4 | 30.6 | 43.4 | 40.9 | 26 | 25.2 | 36.5 | 34.3 |
| Waist size (cm) | 108.8 | 108 | 94.4 | 89.8 | 110.5 | 107 | 92.6 | 90.6 | 98.2 | 96.2 |
| Hip size (cm) | 107.7 | 106.2 | 101.5 | 100.8 | 116.6 | 115.9 | 102.3 | 101 | 106.4 | 105 |
| Ratio of waist/hip | 1.01 | 1.02 | 0.93 | 0.89 | 0.95 | 0.92 | 0.91 | 0.90 | 0.92 | 0.92 |

|  | Subject A6 (height=163cm) | | Subject A7 (height=172cm) | | Subject A8 (height=161cm) | | Subject A9 (height=162cm) | | Subject A10 (height=167cm) | |
|---|---|---|---|---|---|---|---|---|---|---|
|  | 0 week | 12 weeks | 0 week | 12 weeks | 0 week | 12 weeks | 0 week | 12 weeks | 0 week | 12 weeks |
| Weight (kg) | 71.6 | 68.9 | 92.7 | 89.1 | 71 | 68 | 95.2 | 91.4 | 93.3 | 90.5 |
| PIBW (%) | 128.33 | 123.49 | 149.21 | 143.42 | 130.43 | 124.82 | 172.74 | 165.84 | 159.30 | 154.52 |
| BMI (Kg/m2) | 26.95 | 25.93 | 31.33 | 30.12 | 27.39 | 26.23 | 36.27 | 34.83 | 33.45 | 32.45 |
| Body fat rate (%) | 31.3 | 30.8 | 34.6 | 33 | 27.2 | 25.9 | 48.8 | 46.9 | 46.9 | 45.4 |
| Waist size (cm) | 95.2 | 93.8 | 104.9 | 103.3 | 91.1 | 90.5 | 108.8 | 106.4 | 113.1 | 112.3 |
| Hip size (cm) | 98.8 | 97 | 109.8 | 108.2 | 100.8 | 98.8 | 115.5 | 113.6 | 109 | 108.4 |
| Ratio of waist/hip | 0.96 | 0.97 | 0.96 | 0.95 | 0.90 | 0.92 | 0.94 | 0.94 | 1.04 | 1.04 |

[FIG. 2]

| | Comparer B1 (height=158cm) | | Comparer B2 (height=174cm) | | Comparer B3 (height=158cm) | | Comparer B4 (height=174cm) | | Comparer B5 (height=158cm) | |
|---|---|---|---|---|---|---|---|---|---|---|
| | 0 week | 12 weeks | 0 week | 12 weeks | 0 week | 12 weeks | 0 week | 12 weeks | 0 week | 12 weeks |
| Weight (kg) | 72.2 | 70.5 | 85.7 | 83.9 | 94.5 | 93.2 | 98.5 | 97.9 | 79.4 | 78.4 |
| PIBW (%) | 137.72 | 134.48 | 134.79 | 131.86 | 180.26 | 177.78 | 154.92 | 153.88 | 151.46 | 149.55 |
| BMI (Kg/m2) | 28.92 | 28.24 | 28.31 | 27.71 | 37.85 | 37.33 | 32.53 | 32.34 | 31.81 | 31.41 |
| Body fat rate (%) | 33.4 | 31.3 | 37.1 | 36.2 | 48.7 | 47.8 | 42.7 | 42.2 | 37.4 | 36.3 |
| Waist size (cm) | 92.1 | 89.7 | 102.6 | 102.5 | 109.7 | 109.5 | 114.7 | 113.4 | 101.9 | 97.7 |
| Hip size (cm) | 103.1 | 102.4 | 105.3 | 104 | 118.1 | 115.3 | 112.5 | 112.4 | 107 | 106.7 |
| Ratio of waist/hip | 0.89 | 0.88 | 0.97 | 0.89 | 0.84 | 0.95 | 1.02 | 1.01 | 0.95 | 0.92 |

| | Comparer B6 (height=167cm) | | Comparer B7 (height=168cm) | | Comparer B8 (height=161cm) | | Comparer B9 (height=167cm) | | Comparer B10 (height=163cm) | |
|---|---|---|---|---|---|---|---|---|---|---|
| | 0 week | 12 weeks | 0 week | 12 weeks | 0 week | 12 weeks | 0 week | 12 weeks | 0 week | 12 weeks |
| Weight (kg) | 69.8 | 68.9 | 78.7 | 77.4 | 89.3 | 88 | 86 | 84.5 | 89.3 | 87.6 |
| PIBW (%) | 119.18 | 117.64 | 132.78 | 130.58 | 164.05 | 161.66 | 146.84 | 144.45 | 160.05 | 157.00 |
| BMI (Kg/m2) | 25.03 | 24.71 | 27.88 | 27.42 | 34.45 | 33.95 | 30.84 | 30.33 | 33.61 | 32.97 |
| Body fat rate (%) | 23.3 | 22.8 | 36.5 | 35.5 | 40.9 | 40.5 | 39 | 38.3 | 44.4 | 43.2 |
| Waist size (cm) | 87.5 | 87.4 | 98.7 | 97.9 | 105 | 104.2 | 105.7 | 104.3 | 112.5 | 107.7 |
| Hip size (cm) | 100.1 | 99.6 | 103.5 | 102.2 | 112.7 | 110.7 | 107.2 | 106.8 | 109.5 | 109.5 |
| Ratio of waist/hip | 0.87 | 0.88 | 0.95 | 0.96 | 0.93 | 0.94 | 0.99 | 0.98 | 1.03 | 0.98 |

[FIG.3]
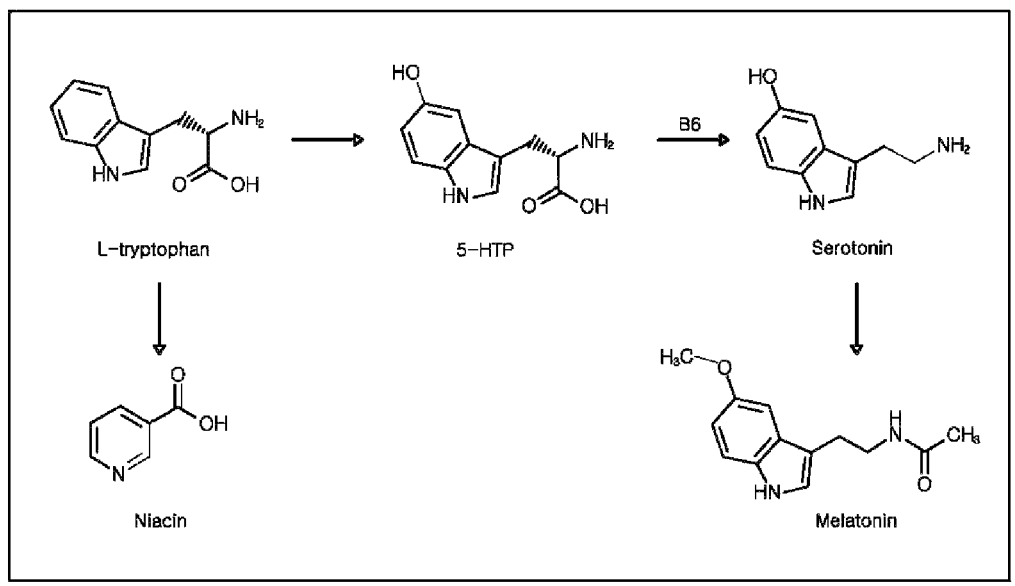
[FIG.4]
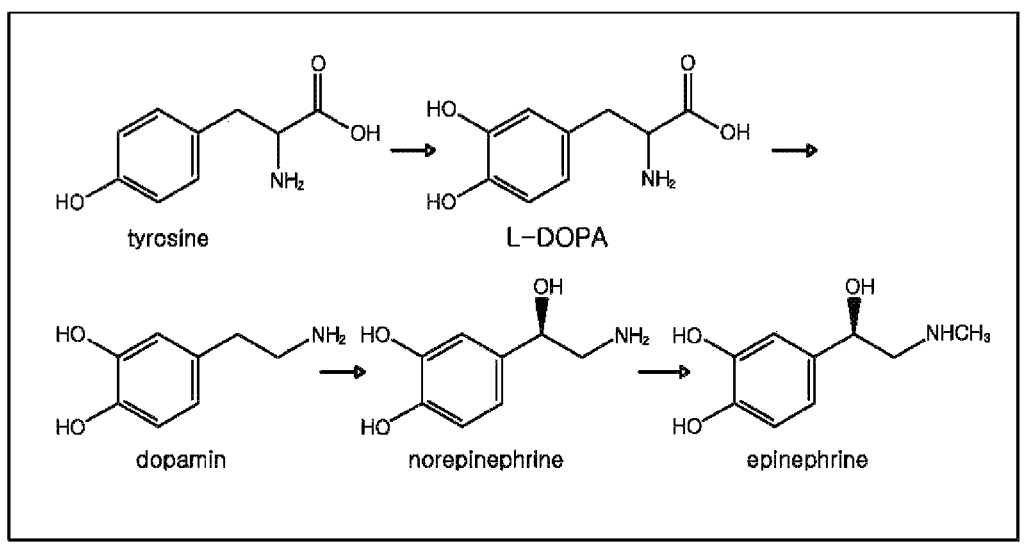

[FIG.5]
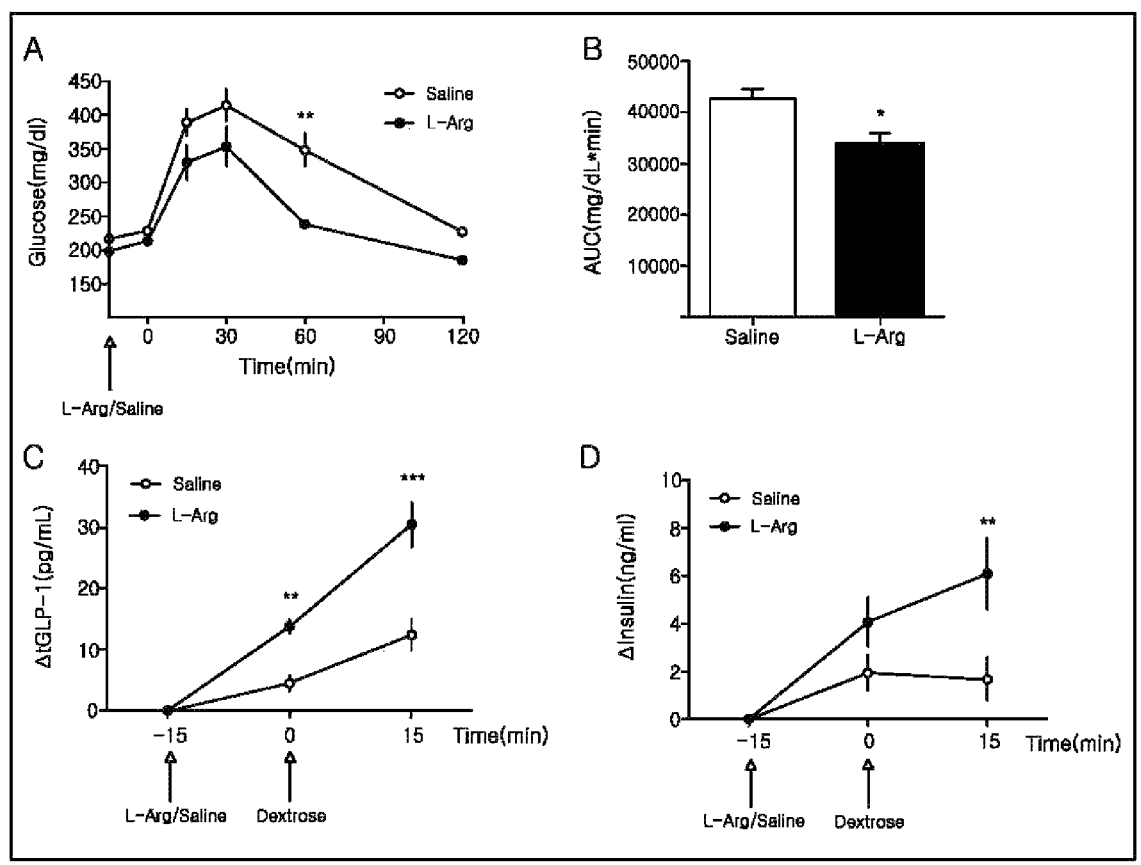

METHOD AND A DIETARY COMPOSITION ON REGULATION, TREATMENT, AND PREVENTION OF OBESITY

TECHNICAL FIELD

The present invention relates to a method and a dietary composition useful for prevention, treatment, and regulation of obesity.

BACKGROUND ART

In the modern society, with the industry development, the quality and convenience of life are greatly improved, while obesity has been caused as a social problem due to the westernization of dietary life, excessive stress, insufficient exercise, etc. According to the 'National Health Statistics' (conducted by Korea Centers for Disease Control and Prevention in the Ministry of Health and Welfare) published in 2019, the obesity prevalence over 19 years of age in Korea was 34.4%, and one of three adults appeared as obesity, and the prevalence of various diseases associated with obesity such as diabetes, hypertrophy, and hypercholesterol, etc. is also very high. As such, obesity is recognized as a serious threat to national health care.

The causes of the obesity in diet are diverse, but commonly, more calorie intake (especially, carbohydrates and fat) than is required and the lack of energy consumption (the lack of exercise, etc.) occupy the main cause. Thus, in contrast, when the weight loss is required, less calorie intake than is required and increased energy consumption (increase in activity or momentum) are required. In particular, in the stressful modern society, the lack of activity or momentum, habitual intake of food (confectionery, snacks, etc.) for stress mitigation, and continuous intake (night eating syndrome) of a large amount of food with relaxation after work are caused, and as a result, weight and body fat are increased, resulting in obesity.

In order to prevent and improve obesity, exercise therapy, drug therapy, or the like is presented. When these methods are appropriately used, obesity is a disease that may be sufficiently regulated. However, it is hard to regulate such because it is difficult to continue to exercise in busy life, and the drug therapy has a risk of serious side effects.

As to a drug therapy, a selective serotonin reuptake inhibitor (SSRI), phentermine, an injection type Saxenda or the like is used. The SSRI (e.g., Prozac, etc.) increases the blood concentration of hormone called serotonin, the phentermine acts to sympathetic nervous system as a sympathetic system acting drug to induce appetite suppression through activation of sympathetic nerves, and the Saxenda acts to GLP-1 in the body as a self-injection (self-injected to the abdomen like an insulin injection) to regulate the appetite. For reference, most (about 90%) of the serotonin in the body is produced and secreted in enterochromaffin cells of the gastrointestinal tract. The serotonin of the gastrointestinal tract has a physiological function such as regulating the gastrointestinal movement. On the other hand, the rest of the serotonin is produced and secreted in serotonergic neurons located in the central nervous system, and is involved in regulation of mood, appetite, sleep, and the like.

However, the drugs used in such a drug therapy are designated as professional medicines requiring a physician's prescription and having a relatively risk. Particularly, phentermine, i.e., a sympathetic nervous drug, is designated as a psychotropic agent (DEA Schedule IV in US), so that access to the drug is not available without the physician's prescription.

DISCLOSURE

Technical Problem

An object of the present invention is to provide a method and a dietary composition useful for prevention, treatment, and regulation of obesity capable of obtaining efficacy such as required appetite suppression or satiety by having a positive effect on concentrations of neurotransmitters such as serotonin, dopamine, and norepinephrine, and GLP-1 which are the principle mechanism of appetite suppressants without prescription of medicines (Phentermine, Prozac®, Saxenda®, etc.) and further being used as an alternative diet and supplying a protein that is the most lack ingredient during diet.

Technical Solution

To achieve the object, a method and a dietary composition useful for prevention, treatment, and regulation of obesity of an embodiment of the present invention includes tryptophan, which is one amino acid, tyrosine, which is the other amino acid, arginine, which is another amino acid, and a whey protein as active ingredients.

Preferably, the dietary composition useful for prevention, treatment, and regulation of obesity according to the embodiment of the present invention may contain 3.6 wt % to 4.6 wt % of the tryptophan, 5 wt % to 6 wt % of the tyrosine, 7.7 wt % to 8.7 wt % of the arginine, and 81 wt % to 83 wt % of the whey protein are contained as the active ingredients.

The dietary composition useful for prevention and regulation of obesity according to the embodiment of the present invention may be administered as a meal replacement.

The dietary composition useful for prevention and regulation of obesity according to the embodiment of the present invention may be prepared in a powder form.

The dietary composition useful for prevention and regulation of obesity according to the embodiment of the present invention may be administered as a meal replacement by mixing the tryptophan powder, the tyrosine powder, the arginine powder and the whey protein powder with water and preparing the mixture in a shake form.

The dietary composition useful for prevention and regulation of obesity according to the embodiment of the present invention may contain 1.5 g of the tryptophan powder, 2 g of the tyrosine powder, 3 g of the arginine powder and 30 g of the whey protein powder as the active ingredients.

Advantageous Effects

As described above, a method and a dietary composition useful for prevention and regulation of obesity according to an embodiment of the present invention may have the following effects.

According to an embodiment of the present invention, there is provided a technical configuration containing tryptophan, which is one amino acid, tyrosine, which is the other amino acid, arginine, which is another amino acid, and a whey protein as active ingredients. Serotonin, an appetite suppression neurotransmitter is synthesized from tryptophan, and dopamine & norepinephrine, which are appetite suppression neurotransmitters are synthesized from tyrosine, and the GLP-1 (which causes satiety) concentration is increased after taking arginine. In addition, since a protein which is an alternative diet nutrient may be supplied from the whey protein, it is possible to obtain efficacy such as required appetite suppression or inducing satiety by having a positive effect on concentrations of neurotransmitters such as serotonin, dopamine, and norepinephrine, and GLP-1 which are the principle of a mechanism of appetite suppressants without prescription of medicines (Phentermine, Prozac®, Saxenda®, etc.). In addition, it is possible to be used as an alternative diet (meal replacement), to supply a protein that is the most lack ingredient during diet, and ultimately, maintain appetite suppression and satiety, and promoting effects of weight regulation and body fat reduction by taking before the meal or taking as a meal replacement for diet.

DESCRIPTION OF DRAWINGS

FIG. 1 illustrates a change in physical index of each of 10 persons in a test group taking a dietary composition useful for prevention and regulation of obesity according to an embodiment of the present invention.

FIG. 2 illustrates a change in physical index of each of 10 persons in a control group taking a comparative food.

FIG. 3 illustrates a process in which serotonin which is an appetite suppression neurotransmitter is synthesized in tryptophan.

FIG. 4 illustrates a process in which dopamine and norepinephrine, which are appetite suppression neurotransmitters, are synthesized in tyrosine.

FIG. 5 shows that L-arginine induces GLP-1 secretion in DIO mice and improves glucose resistance.

BEST MODE

Hereinafter, embodiments of the present invention will be described in detail so as to be easily implemented by those skilled in the art. However, these embodiments are only illustrative of the present invention, and the scope of the present invention is not limited to these embodiments.

A method of preventing and regulating obesity includes a dietary composition. The dietary composition useful for prevention and regulation of obesity according to an embodiment of the present invention includes tryptophan, which is one amino acid, tyrosine, which is the other amino acid, arginine, which is another amino acid, and a whey protein as active ingredients.

In the present invention, it is characterized as a dietary composition having a new composition which includes tryptophan, tyrosine, arginine, and the whey protein as active ingredients, and is taken before the meal or as a meal replacement for diet to maintain appetite suppression and satiety and promote effects of weight regulation and body fat reduction.

The "tryptophan" used in the present invention is an essential amino acid that needs to be ingested from the outside because most animals, including humans can not be synthesized by themselves. The most important role of such tryptophan is used as a raw material of various proteins in vivo. In particular, the tryptophan is used as a precursor of serotonin as a neurotransmitter, melatonin as a sleep hormone, vitamin B3, and NAD, alkaloid, and auxin as a grown hormone of a plant. Therefore, it is known that when meat, chocolate, or the like containing a lot of tryptophan is taken, it is effective in treating depression, and it is effective for alcoholism.

In addition, according to the paper (Nutrition & Diabetes volume 11, Article number: 3, 2021), it has been known that the tryptophan delays the gastric emptying to maintain satiety and act on appetite suppression, like a self-injection appetite suppressant "Saxenda®".

The tryptophan is produced based on the fermentation of serine and indole using wild type or genetic modified bacteria. This strain has a mutation that prevents re-absorption of aromatic amino acids or multiple/overexpressed operon. The conversion is catalyzed by an enzyme, tryptophan synthase.

The process in which serotonin, as the appetite suppression neurotransmitter is synthesized in tryptophan, is as shown in FIG. 3.

In the final process, serotonin and melatonin are helpful in maintaining deep sleep as well as satiety and appetite suppression to be help even in prevention of sleeplessness which is caused in the night eating syndrome. However, since the appetite suppression effect is limited and the satiety cannot be induced with only tryptophan, in addition to tryptophan, tyrosine, arginine, and the whey protein are taken together to promote the effects of weight regulation and body fat reduction.

Further, it is preferable that in the dietary composition useful for prevention, treatment, and regulation of obesity according to the embodiment of the present invention, tryptophan is mixed in an appropriate amount in the range of 3.6 wt % to 4.6 w %. When the content of the tryptophan is less than 3.6 wt %, there is no addition effect for the satiety maintenance and appetite suppression, and when the content of the tryptophan is more than 4.6 wt %, it was not helpful in palatability and productivity due to flavor.

The "tyrosine" used in the present invention is a raw material for dopamine and norepinephrine as a nonessential amino acid and dopamine and norepinephrine act on the sympathetic nervous system to suppress appetite.

Two methods are used to prepare tyrosine. A first method is to extract a desired amino acid from a protein hydrolysate using a chemical approach method and a second method is to use enzyme synthesis of phenol, pyruvate, and ammonia using tyrosine phenol-lyase. With the development of genetic engineering and the introduction of industrial fermentation, synthesis of L-tyrosine is transferred to the use of strains.

A process of synthesizing dopamine and norepinephrine, which are appetite suppression neurotransmitters, in tyrosine, is as illustrated in FIG. 4.

Further, it is preferable that in the dietary composition useful for prevention, treatment, and regulation of obesity according to the embodiment of the present invention, tyrosine is mixed in an appropriate amount in the range of 5 wt % to 6 w %. When the content of the tyrosine is less than 5 wt %, there is no addition effect for the appetite suppression, and when the content of the tyrosine is more than 6 wt %, it was not helpful in palatability and productivity due to flavor.

The "arginine" used in the present invention is one of amino acids and increases the secretion of GLP-1, which shows satiety and appetite suppression effects eve in the humans.

As illustrated in FIG. 5, it was found that L-arginine induces GLP-1 secretion in DIO mice and improves glucose resistance. Here, FIG. 5A illustrates glucose after orally administering L-arginine (1 g/kg) or saline in DIO C57BL/6 mice before 15 minutes of OGTT (2 g glucose/kg bw) (2-directional repeat measurement ANOVA, N 4-5), FIG. 5B illustrates a glucose area (AUC) (t test) under a curve, FIG. 5C illustrates plasma total GLP-1 reaction (TGLP-1) for oral tube of L-arginine or saline before 15 minutes of OGTT (2 g dextrose/kg bw) in DIO mice (2-directional repeat measurement ANOVA, n 9), and FIG. 5D illustrates a plasma insulin reaction (insulin) after orally administering L-arginine or saline before 15 minutes of OGTT (2 g glucose/kg bw) in DIO mice (2-directional repeat measurement ANOVA, n 9).

On the other hand, arginine is described well in the satiety effect of proteins compared to other nutrients and is partially mediated by long-hormone release. Previously, it was found that oral L-arginine acts as a GLP-1 secretion accelerator in both the test tubes and in vivo in the rodent. Here, the effect of L-arginine for human intestine hormone release was examined. To this end, a hypothesis was tested in two individual studies. A first study evaluated the drug tolerance of oral L-arginine for healthy people. The second study evaluated the effects of oral L-arginine for the intestine hormone release after unlimited meals. Subjects to be tested received L-arginine, glycine (control amino acid) or a vehicle control by a double-blind fashion. As a result, in a capacity of 17.1 mmol, L-arginine was excellent in drug tolerance and after unlimited meals, and the release of plasma GLP-1 (p<0.05) and PYY (p<0.001) was stimulated. Food diary showed less energy intake, particularly less fat intake after L-arginine treatment. As a result, it could be seen that L-arginine greatly increased the GLP-1 and PYY of healthy human volunteers with meals (Obesity/Volum 26. Issue 11/p. 1721-1726).

Further, it is preferable that in the dietary composition useful for prevention, treatment, and regulation of obesity according to the embodiment of the present invention, the arginine is mixed in an appropriate amount in the range of 7.7 wt % to 8.7 w %. When the content of the arginine is less than 7.7 wt %, there is no addition effect for the increased secretion of GLP-1 showing the satiety and appetite suppression effects, and when the content of the arginine is more than 8.7 wt %, it was not helpful in palatability and productivity due to flavor. For reference, in the case of administration of 17.1 mmol, the secretion of GLP-1 (appetite suppression hormone) was increased, and as a result of calculating the effect with a molecular weight of 174.2 g/mol of arginine, about 3 g may increase most effectively GLP-1.

The whey protein accounts for approximately 20% of milk proteins with proteinoid from which casein is removed and supplies a protein as an essential nutrient as an alternative diet (meal replacement) and increases the blood concentration of a specific amino acid in a degradation process in vivo even as a whey protein itself to increase the appetite suppression effect of obese people and satiety by promoting GLP-1.

Further, it is preferable that in the dietary composition useful for prevention and regulation of obesity according to the embodiment of the present invention, the whey protein is mixed in an appropriate amount in the range of 81 wt % to 83 w %. When the content of the whey protein is less than 81 wt %, there is no addition effect for the appetite suppression and satiety maintenance, and when the content of the whey protein is more than 83 wt %, the amount of arginine, etc. was relatively reduced, and the rising effect on weight loss was not large.

As described above, it has been known that each active ingredient of tryptophan, tyrosine, arginine and the whey protein has a functionality associated with appetite suppression or satiety, but there is a limit to exhibit a comprehensive diet effect. That is, in order to show the comprehensive diet effect, the dietary composition should be able to induce excellent appetite suppression and excellent satiety even in a small amount of intake. In particular, tryptophan, which synthesizes serotonin as an appetite suppression neurotransmitter, tyrosine which synthesizes dopamine and norepinephrine as appetite suppression neurotransmitters, arginine which increases the secretion of GLP-1 showing satiety and appetite suppression effects, and a whey protein which is excellent for satiety induction and supplies a protein which is an alternative diet nutrient are particularly selected. When these ingredients are taken together, it may be experimentally confirmed that the effect was more increasing due to the synergistic action therebetween, and it was found that the alternative diet is also possible.

Further, in order to maximize the appetite suppression and satiety of the dietary composition useful for prevention and regulation of obesity according to the embodiment of the present invention, it is required to optimize a content ratio of tryptophan, tyrosine, arginine and the whey protein. Preferably, the dietary composition useful for prevention, treatment, and regulation of obesity according to the embodiment of the present invention has a content ratio of 3.6 wt % to 4.6 wt % of tryptophan, 5 wt % to 6 wt % of tyrosine, 7.7 wt % to 8.7 wt % of arginine and 81 wt % to 83 wt % of the whey protein.

Further, the dietary composition useful for prevention, treatment, and regulation of obesity according to the embodiment of the present invention may be prepared in a powder form according to a general method known in the art. In addition, the user may mix the dietary composition in a powder form with water and take the dietary composition in a shake form before the meal or as a meal replacement. For example, 1.5 g of tryptophan powder, 2 g of tyrosine powder, 3 g of arginine powder and 30 g of whey protein powder are mixed with 200 ml of water and prepared and taken in a shake form.

Subsequently, Experimental Examples using the dietary composition useful for prevention, treatment, and regulation of obesity according to the embodiment of the present invention will be described.

<Experimental Examples>

Powder was provided with a composition shown in Table 1.

TABLE 1

| | <Powder> | |
|---|---|---|
| | Comparative Food (Powder)- | Present Food (Powder)- |
| | Group B | Group A |
| Name of raw material | (Control Group) | (Test Group) |
| Tryptophan Powder | — | 15 g |
| Tyrosine powder | — | 2 g |
| Arginine powder | — | 3 g |
| Whey protein powder | 30 g | 30 g |
| Total amount of the dietary composition | 30 g | 36.5 g |

Human Clinical Trial for Obesity Suppression Effect

An obesity suppression effect of the dietary composition useful for prevention, treatment, and regulation of obesity according to the embodiment of the present invention was confirmed through a clinical trial. Subjects to be tested were publicly collected as volunteers for overweight or abdominal obesity adults of 19 to 60 years of age having 110% or more of PIBW (percent of ideal body weight), 80 cm or more of the waist size, and a body mass index (BMI) of 25 or higher.

Total 20 volunteers were divided into two groups of 10 persons, wherein in one group (Group A), the present food (test group) of Table 1 was supplied and in the other group (Group B), a comparative food (control group) was supplied. In each group, the powder of the above composition (Table 1) was mixed in 200 ml of water at 5-6 pm once a day in the form of a shake and administered daily for 12 weeks.

A result of measuring and comparing changes in body index before and after administration of the present food was as shown in Table 2 below. In the test group, it was shown that changes in all body indexes such as PIBW, BMI, body fat rate, and waist size were decreased. On the contrary, in the control group, the test was conducted while the takers did not know the control group, the powder containing only the whey protein was supplied (as shown in Table 1), and there was an appetite suppression effect by the whey protein itself. As a result, after 12 weeks, there was a little weight loss, but it was found that the weight loss was made much less than the takers of the present food.

For reference, the size and the body fat amount were measured using a body composition analyzer, INBODY, and FIG. 1 illustrates changes in body index of each of 10 persons in a test group and FIG. 2 illustrates changes in body index of each of 10 persons in a control group.

TABLE 2

| <Changes in body index before and after taking> | | | | |
|---|---|---|---|---|
| | Group A (test group) (n = 10) | | Group B (control group) (n = 10) | |
| | 0 week | 12 weeks | 0 week | 12 weeks |
| Weight (kg) | 83.96 ± 11.40 | 81.06 ± 11.19 | 84.34 ± 8.79 | 83.04 ± 8.85 |
| PIBW (%) | 146.89 ± 15.14 | 141.79 ± 14.74 | 148.21 ± 16.87 | 145.91 ± 16.81 |
| BMI (Kg/m$^2$) | 30.85 ± 3.18 | 29.78 ± 3.09 | 31.12 ± 3.54 | 30.64 ± 3.53 |
| Body fat rate (%) | 36.65 ± 7.48 | 34.98 ± 7.13 | 38.34 ± 6.53 | 37.41 ± 6.57 |
| Waist size (cm) | 101.76 ± 7.88 | 99.79 ± 8.07 | 103.04 ± 8.14 | 101.43 ± 7.91 |
| Hip size (cm) | 106.84 ± 5.79 | 105.49 ± 5.91 | 107.70 ± 4.74 | 106.96 ± 4.75 |
| Ratio of waist/hip | 0.95 ± 0.04 | 0.95 ± 0.05 | 0.96 ± 0.05 | 0.95 ± 0.04 |

The effect after taking started to induce satiety from about 30 minutes, and its effect continued for 6 hours to 12 hours. As shown in Table 2, all of weight, PIBW, BMI, body fat rate, waist size, hip size, and ratio waist/hip in Group A were reduced more compared to Group B. In addition, the time to sleep and the sleep quality were improved, and the frequency of waking-up was reduced (the effect of increasing serotonin and melatonin by the tryptophan ingredient). In addition, as a complex effect of each amino acid, the amount of food intake was reduced due to the decrease in the desire to take food and early satiety during food taking.

Meanwhile, in other experiments, in the case of patients with the night eating syndrome, when this formulation was taken at 5 to 6 p.m., while the food taken in the evening was decreased, naturally, the food was induced to be taken in a day time at the next day. Next day, due to a synergic effect of the food taken in a day time and the dietary composition of the present invention taken at 5 to 6 p.m., thereafter, while the amount of food intake was reduced to the time of sleep, a virtuous circle structure has been made, and at the same time, a good-quality sleep may be obtained by secretion of serotonin and melatonin by tryptophan.

On the other hand, if there is a problem in overtaking of food in a day time, it was confirmed through another experiment that when administering before a lunch (about 12 o'clock), the amount of intake is reduced from lunch and snacks were not taken or the amount thereof was reduced in the afternoon, the amount of dinner was reduced to enable an effective diet.

While the preferred embodiment of the present invention has been described in detail, the scope of the present invention is not limited thereto, and various modifications and improvements of those skilled in the art using a basic concept of the present invention defined in the appended claims also belong to the scope of the present invention.

The invention claimed is:

1. A method of treating and regulating obesity, comprising:
administering a therapeutically effective amount of a dietary composition comprising therapeutically effective amounts of tryptophan, tyrosine, arginine, and a whey protein, as active ingredients to an obese or overweight subject in need thereof to treat the obesity, wherein 3.6 wt % to 4.6 wt % of the tryptophan, 5 wt % to 6 wt % of the tyrosine, 7.7 wt % to 8.7 wt % of the arginine, and 31 wt % to 83 wt % of the whey protein are contained in the dietary composition.

2. The method of claim 1, wherein the dietary composition is administered to the subject as a meal replacement.

3. The method of claim 1, wherein the dietary composition is prepared in a powder form.

4. The method of claim 3, wherein the dietary composition is administered to the subject as a meal replacement by mixing a tryptophan powder, a tyrosine powder, an arginine powder and a whey protein powder with water and preparing the mixture in a shake form.

* * * * *